US009282934B2

(12) United States Patent
Liley et al.

(10) Patent No.: US 9,282,934 B2
(45) Date of Patent: Mar. 15, 2016

(54) COMPOSITE BRAIN FUNCTION MONITORING AND DISPLAY SYSTEM

(75) Inventors: David Tibor Julian Liley, Yarraville (AU); Nicholas Campbell Sinclair, Surrey Hills (AU)

(73) Assignee: Cortical Dynamics Limited (AU)

( * ) Notice: Subject to any disclaimer, the term of this patent is extended or adjusted under 35 U.S.C. 154(b) by 534 days.

(21) Appl. No.: 13/822,328

(22) PCT Filed: Sep. 21, 2011

(86) PCT No.: PCT/AU2011/001222
§ 371 (c)(1),
(2), (4) Date: Apr. 30, 2013

(87) PCT Pub. No.: WO2012/037610
PCT Pub. Date: Mar. 29, 2012

(65) Prior Publication Data
US 2013/0317380 A1    Nov. 28, 2013

(30) Foreign Application Priority Data

Sep. 21, 2010  (AU) ................. 2010904259

(51) Int. Cl.
*A61B 5/04*    (2006.01)
*A61B 5/00*    (2006.01)
*A61B 5/0476*  (2006.01)

(52) U.S. Cl.
CPC .............. *A61B 5/743* (2013.01); *A61B 5/04012* (2013.01); *A61B 5/0476* (2013.01); *A61B 5/7282* (2013.01); *A61B 5/7253* (2013.01); *A61B 5/7435* (2013.01)

(58) Field of Classification Search
None
See application file for complete search history.

(56) References Cited

U.S. PATENT DOCUMENTS

| 2006/0135879 A1 | 6/2006 | Liley et al. |
| 2010/0204604 A1 | 8/2010 | Liley et al. |

FOREIGN PATENT DOCUMENTS

| EP | 0898234 A1 | 2/1999 |
| WO | 9624128 A1 | 8/1996 |
| WO | 0174248 A1 | 10/2001 |
| WO | 2004054441 A1 | 7/2004 |
| WO | 2004064633 A1 | 8/2004 |

OTHER PUBLICATIONS

Messner et al., "The Bispectral Index Declines During Neuromuscular Block in Fully Awake Person" Anesth Analg, 2003, 97, pp. 488-491.
Rudolph et al., "Molecular and Neuronal Substrates for General Anaesthetics, Nature Reviews, Neuroscience" Sep. 2004, pp. 709-720.
Tarvainen et al., "Estimation of Nonstationary EEG with Kalman Smoother Approach: An Application to Event Related Synchronization (ERS)" IEEE Trans Biomed Eng, Mar. 2004, pp. 516-524.
P. Broersen., "Autoregressive Model Orders for Durbin's MA and ARMA Estimators," IEEE Transactions on Signal Processing, 2000, vol. 48 (8), pp. 2454-2457.

*Primary Examiner* — Etsub Berhanu
(74) *Attorney, Agent, or Firm* — Banner & Witcoff, Ltd.

(57) ABSTRACT

A method of displaying the activity of a brain, the method including the steps of: (i) obtaining an electroencephalogram (EEG) signal from the brain; (ii) segmenting said EEG signal into either contiguous or overlapping segments comprised of a sequential number of samples of said EEG signal; (iii) representing said EEG segments as a fixed order autoregressive moving average (ARMA) signal representation with an autoregressive order between 8 and 13 and a moving average order between 5 and 11; (iv) rewriting in z-domain notation said fixed order ARMA signal representation to obtain a z-domain representation; (v) generating AR coefficient data and MA coefficient data for said segments of said EEG signal for said fixed order ARMA signal representation: (vi) determining the poles and zeros of said z-domain representation for said segments of said EEG signal by substituting said coefficient data for said segments of said EEG signal into said z-domain representation; (vii) calculating the sum of the number of poles determined in step (vi); (viii) calculating the sum of the number of zeros determined in step (vi); (ix) representing said ARMA signal representation as an infinite order autoregressive (AR) model in z-domain notation; (x) determining autoregressive coefficient data for said infinite AR model from the AR and MA coefficient data generated in step (v) of said fixed order ARMA representation; (xi) determining the sum of the poles for said infinite order AR model for said segments of said EEG signal as either: (a) the first autoregressive coefficient of said finite order AR model; or (b) the difference of the sum of poles and the sum of zeros as determined respectively in steps (vii) and (viii); (xii) determining an index value representing the activity of the brain for said segments of said EEG signal by applying a discriminating function to the sum of the poles of said infinite AR model for said segments of said EEG signal as determined in step (xi); and (xiii) displaying said index value on display means.

22 Claims, 6 Drawing Sheets

COMPOSITE BRAIN FUNCTION MONITORING AND DISPLAY SYSTEM

RELATED APPLICATION DATA

This application is a National Stage Application under 35 U.S.C. 371 of co-pending PCT application PCT/AU2011/001222 designating the United States and filed Sep. 21, 2011; which claims the benefit of AU patent application number 2010904259 and filed Sep. 21, 2010 each of which are hereby incorporated by reference in their entireties.

FIELD

The present invention relates to a process and system for monitoring brain function based on cortical responsive state and cortical neuronal input.

BACKGROUND

A process for quantifying brain function may involve analysing the spontaneous or stimulus locked scalp recordable electrical activity from a subject. For example, this includes analysing the waveform of early, middle and/or late stimulus evoked components (e.g. as described in International Patent Publication WO 2001/74248); or spectral analysis of spontaneously recorded activity (not in response to a particular or general stimulus) using frequency or time domain methods (e.g. as described in European Patent Application EP0898234); or a hybrid approach in which both spontaneous and evoked EEG activity is analysed to determine brain state (e.g. as described in International Patent Publication WO 2004/054441).

While such methods have been shown to have clinical efficacy when appropriately constructed statistical discriminant functions are employed, it is unclear what physiological aspects of behaviour and brain function such measures reflect. For instance, these approaches may be detecting changes in EMG activity, and not EEG activity. The Messner report (published in Anesth Analg, 2003, 97, pp. 488-491) describes how the bispectral index declines during neuromuscular blockade in fully awake persons. Recent theoretical and experimental work by Liley et al (as described in International Patent Publication WO 2004/064633) proposes a specific theoretical framework that enables the construction of more physiologically specific measures of brain function. This framework enables greater structural and functional specificity in representing changes in cortical activity induced by a variety of internal and external factors.

In assessing a subject's brain function such as, for instance, during health, disease and/or therapeutic intervention, or for the purpose of controlling or interfacing with some external hardware device such as a computer when used for control or entertainment purposes, it is important to distinguish the factors that give rise to changes in brain function. For example, this includes changes in brain (cortical) state (i.e. the brain's inherent receptivity to input from subcortical or distant cortical sources) and changes in the level of cortical neuronal input (which may occur as a consequence of altered input to the cerebral cortex). While an analysis of the early components of a variety of event related potentials (ERP) may provide information regarding the integrity of the various input pathways to the cortex, this technique is inherently limited as not all cortical areas are the recipient of peripherally derived sensory information. For example, the frontal cortex neither directly nor indirectly (through subcortical nuclei) receives any sensory information. Another limitation of this approach is that, in order to obtain a sufficient signal-to-noise ratio, the evoked response of a number of sequentially presented stimuli must be determined, which clearly limits the temporal resolution of the results obtained. However, there are methods that attempt to improve the temporal resolution by using some form of forecasting method (e.g. as described in International Patent Publication WO2001/74248).

Quantitative EEG (QEEG) methods involving spectral analysis using time or frequency domain methods (e.g. as described in European Patent Application EP0898234) are unable to distinguish between changes in cortical input and brain (cortical) state, because such techniques are unable to make assumptions regarding the physiological sources of changes in EEG spectral power. This is principally a consequence of the heuristic approach of current QEEG methods.

Accordingly, it is difficult to determine whether changes in EEG signals from a subject are caused by changes in cortical input (e.g. to different areas of the brain), or are a consequence of qualitative and quantitative changes in how the cortex responds to this input. There is also no satisfactory way for representing changes in a subject's brain function based on changes in cortical responsive state and the level of cortical neuronal input.

It is desired to address one or more of the above, or to provide at least a useful alternative.

SUMMARY OF INVENTION

According to the present invention there is provided a method of displaying the activity of a brain, the method including the steps of:

(i) obtaining an electroencephalogram (EEG) signal from the brain;

(ii) segmenting said EEG signal into either contiguous or overlapping segments comprised of a sequential number of samples of said EEG signal;

(iii) representing said EEG segments as a fixed order autoregressive moving average (ARMA) signal representation with an autoregressive order between 8 and 13 and a moving average order between 5 and 11;

(iv) rewriting in z-domain notation said fixed order ARMA signal representation to obtain a z-domain representation;

(v) generating AR coefficient data and MA coefficient data for said segments of said EEG signal for said fixed order ARMA signal representation;

(vi) determining the poles and zeros of said z-domain representation for said segments of said EEG signal by substituting said coefficient data for said segments of said EEG signal into said z-domain representation;

(vii) calculating the sum of the number of poles determined in step (vi);

(viii) calculating the sum of the number of zeros determined in step (vi);

(ix) representing said ARMA signal representation as an infinite order autoregressive (AR) model in z-domain notation;

(x) determining autoregressive coefficient data for said infinite AR model from the AR and MA coefficient data generated in step (v) of said fixed order ARMA representation;

(xi) determining the sum of the poles for said infinite order AR model for said segments of said EEG signal as either:

(a) the first autoregressive coefficient of said infinite order AR model; or (b) the difference of the sum of poles and the sum of zeros as determined respectively in steps (vii) and (viii);

(xii) determining an index value representing the activity of the brain for said segments of said EEG signal by applying a discriminating function to the sum of the poles of said infinite AR model for said segments of said EEG signal as determined in step (xi); and (xiii) displaying said index value on display means.

The present invention also provides computer executable code stored on computer readable medium to perform any of the steps in a process as described above.

The present invention also provides a system for performing a process as described above.

The present invention also provides a system for displaying the activity of a brain of a subject, the system including:

a plurality of electrodes for picking up EEG signals from the brain of the subject;

digitising means for converting the EEG signals to a digitised EEG data signal; computing means for:

(i) segmenting said EEG signal into either contiguous or overlapping segments comprised of a sequential number of samples of said EEG signal:

(ii) representing said EEG segments as a fixed order autoregressive moving average (ARMA) signal representation with an autoregressive order between 8 and 13 and a moving average order between 5 and 11;

(iii) rewriting in z-domain notation said fixed order ARMA signal representation to obtain a z-domain representation;

(iv) generating AR coefficient data and MA coefficient data for said segments of said EEG signal for said fixed order ARMA signal representation;

(v) determining the poles and zeros of said z-domain representation for said segments of said EEG signal by substituting said coefficient data for said segments of said EEG signal into said z-domain representation;

(vi) calculating the sum of the number of poles determined in step (v);

(vii) calculating the sum of the number of zeros determined in step (v);

(viii) representing said ARMA signal representation as an infinite order autoregressive (AR) model in z-domain notation;

(ix) determining autoregressive coefficient data for said infinite AR model from the AR and MA coefficient data generated in step (iv) of said fixed order ARMA representation;

(x) determining the sum of the poles for said infinite order AR model for said segments of said EEG signal as either:

(a) the first autoregressive coefficient of said infinite order AR model; or (b) the difference of the sum of poles and the sum of zeros as determined respectively in steps (vi) and (vii).

(xi) determining an index value representing the activity of the brain for said segments of said EEG signal by applying a discriminating function to the sum of the poles of said infinite AR model for said segments of said EEG signal as determined in step (x); and (xii) generating display data for displaying said index value on display means.

BRIEF DESCRIPTION OF THE DRAWINGS

A preferred embodiment of the present invention is herein described, by way of example only, with reference to the accompanying drawings, wherein.

DETAILED DESCRIPTION OF THE PREFERRED EMBODIMENTS

Figure 1:
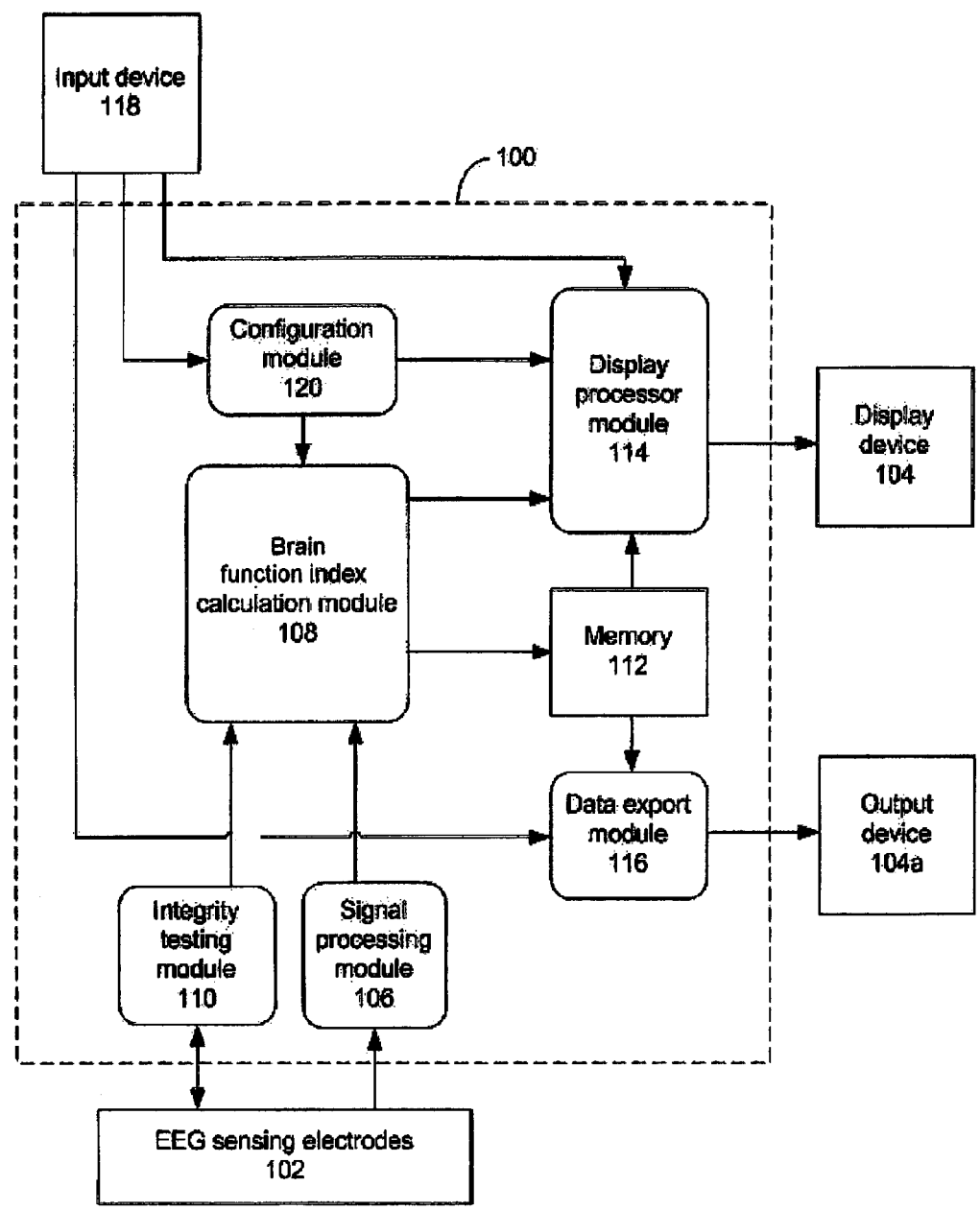
FIG. 1 is a block diagram of the components in the EEG processing system.

The electroencephalogram (EEG) processing system 100, as shown in FIG. 1, includes a signal processing module 106, brain function index calculation module 108, integrity testing module 110, memory module 112, display processor module 114, data export module 116, and configuration module 120. The modules 106 and 110 are coupled to a plurality of scalp electrodes 102 placed on the subject's scalp. The electrodes 102 are positioned on the subject's scalp in accordance with the international 10:20 standard system, and may include use of additional mid-point electrodes as required. For example, the electrodes 102 may be attached to a strip that positions the electrodes relative to a mid-point of the subject's forehead. Whilst the electrodes 102 are preferably referenced to linked ears and are attached to an electrode cap that uses the nasion as a ground, other electrode arrangements can be used. The electrodes 102 detect an EEG signal from the subject's scalp, which is then received and processed by the EEG processing system 100.

The components of the EEG processing system 100 may be implemented in software and executed on a standard computer (such as that provided by IBM Corporation <http://www.ibm.com>) running a standard operating system (such as Microsoft Windows™ or Unix). Those skilled in the art will also appreciate that the processes performed by the components can also be executed at least in part by dedicated hardware circuits, e.g., Application Specific Integrated Circuits (ASICs) or Field-Programmable Gate Arrays (FPGAs). The components of the system 100 may be implemented as a combination of hardware, embedded firmware and software.

The signal processing module 106 receives and amplifies an EEG signal detected by the electrodes 102, and performs preliminary signal artefact rejection by filtering low frequency movement artefact, electromyogram (EMG) artefact and/or mains interference noise (generally ranging from 20 Hz to 75 Hz) from the EEG signal. For example, the module 106 may filter the detected EEG signal using a 50-60 Hz notch filter before applying a band-pass filter (e.g. a low-pass filter) to the signal somewhere on the range 0 Hz to 60 Hz. The module 106 then generates digital samples representative of the EEG signal using standard analog-to-digital conversion components. The EEG signal may be digitised at a fixed rate (such as between 128 to 512 samples per second), and preferably, at no less than 14-bit resolution.

The brain function index calculation module 108 may perform further signal artefact rejection and other signal preprocessing, including removing additional artefacts from the digital EEG signal not removed by the signal processing module 106 which may compromise the subsequent estimation of the ARMA model coefficients. This involves further removing 50-60 Hz mains contamination using a variety of means or algorithms, such as least mean square adaptive filtering.

The brain function index calculation module 108 then stores the samples in memory 112 and processes the samples in accordance with a processing option selected by the user. A user may select a processing option that controls the brain function index calculation module 108 to store samples generated for an EEG recording session, and to retrieve and process the stored samples. The processing performed by module 108 involves generating a plurality of segments, each including a predetermined number of sequential samples (e.g. representative of a 2-second portion of the EEG signal). Module 108 may generate segments based on an incremental (or "sliding window") approach, for example, by generating a new segment at predetermined time intervals so that each new segment includes one or more new samples generated by the signal processing module 106 as well as samples previously generated by the module 106. Module 108 generates, based on the respective samples for each segment, a time invariant autoregressive moving average (ARMA) representation of the EEG signal for each segment (e.g. based on Equation 2). Module 108 then generates brain response data for each segment based on the respective time invariant ARMA representations.

The brain response data for each segment/EEG sample point includes (i) coefficient data representing autoregressive (AR) coefficients and moving average (MA) coefficients: (ii) pole data representing the position of one or more poles on a complex plane determined based on the coefficient data; (iii) zero data representing the position of one or more zeros on a complex plane determined based on the coefficient data; (iv) mean pole data representing a mean position of poles determined from the poles data; and (v) composite pole-zero data representing the combined mean position of the poles and zeros determined based on the coefficient data.

The mean pole data and composite pole-zero data provide complementary, but distinct, measures of the responsiveness of the cortex to its incoming input, and have been found to provide meaningful measures of the dynamical state of the cortex. The mean pole data and the composite pole-zero data will be referred to as the cortical state and the composite cortical state respectively. The cortical state and composite cortical state, obtained from the analysis of appropriately recorded EEG, may be scaled to fall within a predefined range (e.g. from 0 to 100 inclusive, based on Equations 13 or 14 below). For example a larger value can be defined as representing a higher level of responsiveness of the cortex to its input, and a smaller value represents a less responsive state.

The user may select a different processing option that controls the brain function index calculation module 108 to store the samples in memory 112 and to process the samples based on a recursive approach. The processing performed by module 108 involves generating a time varying ARMA representation of a portion of the EEG signal for each sequential sample point of the EEG signal. A sample point may correspond to each respective sample generated by module 106, or alternatively, module 108 selects new sample points at predetermined time intervals. Module 108 generates coefficient data for each sample point respectively based on a fixed order time varying ARMA representation of the EEG signal that depends on the sampled EEG signal values for the current sample point and for a number of previous sample points, and the coefficient data corresponding to the previous EEG sample point, in a recursive manner (e.g. based on Equation 3 below). Module 108 then generates poles data, zeros data, cortical state data and composite cortical state data for each sample point based on the corresponding coefficient data for that sample point.

The processing performed by module 108 includes generating AR coefficients and MA coefficients for the ARMA representation for each segment/sample point, and each of the ARMA representations has an AR order of between 8 and 14 and a MA order between 5 and 11. However, the ARMA representation preferably has an AR order of 8 and MA order of 5. The AR and MA coefficients generated for each segment/sample point enables the corresponding ARMA representations (when using the AR and MA coefficients as parameters) to represent the EEG signal for the corresponding segment/sample point.

The samples in each segment represent a different portion of the EEG signal, and the samples in adjacent segments may overlap and represent a common portion of the EEG signal. For example, a segment may include 50% of the samples included in another segment immediately preceding it. The degree of overlap of samples in adjacent segments may vary, and a greater degree of overlap (e.g. having more than 50% of the samples in common) enables better estimation of the AR and MA coefficients. Thus, a more accurate representation of the subject's brain function and/or the level of subcortical input/activity can be provided on the basis of the AR and MA coefficients.

The brain function index calculation module 108 then generates brain function index data for each segment/sample point based on the corresponding cortical state, composite cortical state and cortical input data, and stores the index data in memory 112. The cortical input data represents a product value which represents the level of cortical input to the subject's brain, and which is generated based on the EEG samples, coefficient data, and ARMA representation for the corresponding segment/sample point. The cortical input data may be scaled to fall within a predefined range (e.g. from 0 to 100 inclusive, based on Equations 13 or 14). For example a larger value represents a greater level of cortical input to the subject's brain, and a smaller value represents a lower level of cortical input.

The brain function index data represents an index number that represents the functional state of the subject's brain (i.e. the way in which the brain responds to subcortical input and the magnitude of the subcortical input to the brain) and which is generated based on the cortical input data, cortical state data and/or composite cortical state data. The index number may be scaled to fall within a predefined range (e.g. from 0 to 100 inclusive, based on Equations 13 or 14). For example a decrease or inhibition of brain function (e.g. caused by introducing an anaesthetic or analgesic agent to the subject that decreases cortical response and/or cortical neuronal input) results in module 108 generating a small index number to represent a lower functional state of the brain. For example, an index number of 0 represents no functional brain activity. Where brain function is normal or is uninhibited (e.g. during a normal alert state of mind without interventions affecting the cortex), this results in module 108 generating a large index number to represent a higher functional state of the brain. For example, an index number of 100 represents the brain at a fully awake state. Changes in the functional state of the subject's brain can be determined by the changes in the value of the index number for different segments/windows. An advantage of the present invention is that the assessment of brain function of a subject takes into account the degree of brain activity caused by the responsive state of the cortex and that caused by the level of input to cortex.

The brain function index calculation module 108 passes the brain function index data, cortical state, composite cortical state and cortical input data (collectively referred to as brain function data) to the display processor module 114 for generating display data representing one or more user interface displays for the display device 104 (e.g. a CRT or LCD display). The display processor module 114 may receive user input from an input device 118 (e.g. a multi-key data entry device or mouse) whilst generating display data for the display device 104. In one embodiment, the input device 118 and display device 104 are combined into one I/O device (e.g. a touch screen display) so that the display processor module 114 receives user input from, and sends display data to, the same I/O device. The display processor module 114 may also generate one or more display interfaces based on the brain function data retrieved from memory 112. FIGS. 3 to 9 are examples of user interface displays generated by module 114.

Figure 3:
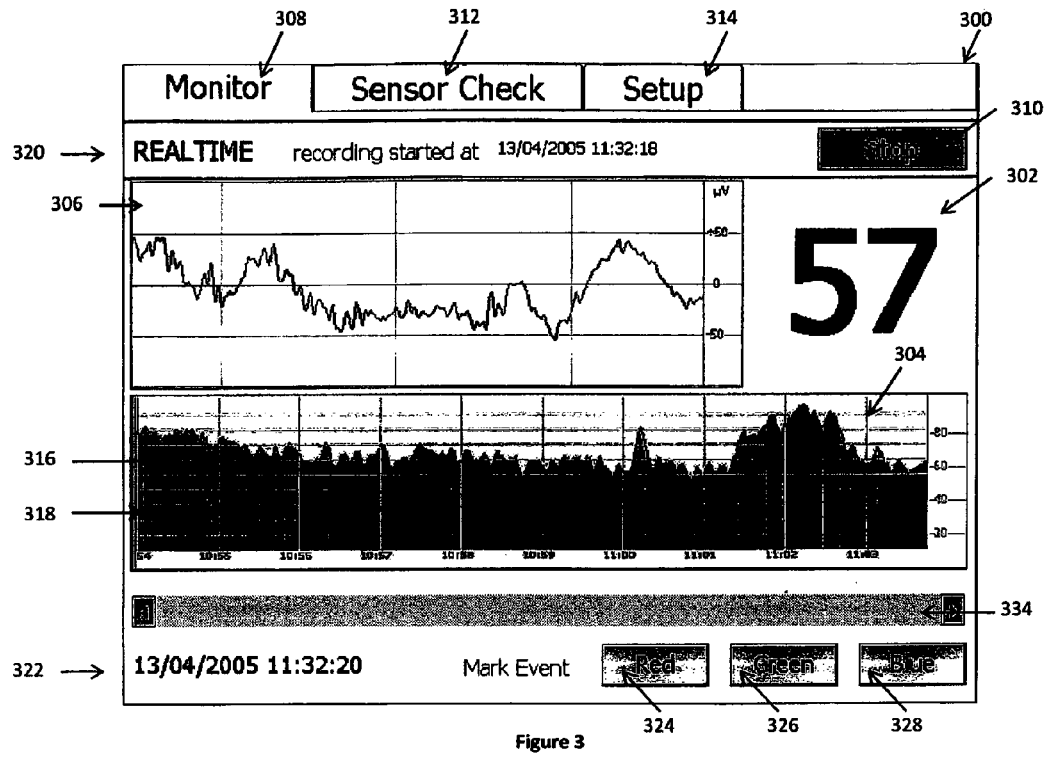
FIG. 3 is an EEG recording interface of the system.

FIG. 3 is an EEG recording interface 300 generated by the display module 114 when the processing an EEG signal using the sliding windows option. The interface 300 includes a monitor tab 308, sensor check tab 312 and setup tab 314 for accessing user interfaces associated with different functions performed by the EEG processing system 100. The interface 300 is generated under the monitor tab 308, and includes a brain function index 302 generated based on the brain function data, a brain function graph 304 representing changes in the value of the brain function index 302 over time, and an EEG graph 306 representing the detected EEG signal generated based on the EEG samples. The interface 300 includes a control button 310 that enables a user to start and stop an EEG recording/monitoring session performed by the EEG processing system 100. The interface 300 also includes fields for displaying information, such as a date/time field 322 displaying the current date/time, and a status field 320 for displaying the processing option selected by the user and the creation date/time for the record data currently displayed on the interface 300. The interface 300 includes an adjustable scroll bar 334 which enables a user to select a viewing portion of graphs 304 and/or 306 for display on the interface 300.

The interface 300 may include one or more event marker buttons 324, 326, 328 for recording an event associated with each respective button. For example, button 324 may be used for indicating the time at which the subject loses consciousness under anaesthesia, and button 326 may be used for indicating the time at which the subject regains consciousness. Each button 324, 326, 328 is associated with a different colour, and when a button 324, 326, 328 is selected by the user, a line of the corresponding colour is generated on the brain function graph 304 corresponding to the time at which the button was operated. The time positions of events recorded on the brain function graph 304 are stored in memory 112.

The brain function graph 304 of the recording interface 300 is generated based on the brain function index 302 such that a portion of the graph 304 is generated for display in a colour corresponding to a predetermined range of brain function index 302 values, where each predefined range is represented by a different colour. For example, if the index 302 is between 0 and 20 (inclusive), the corresponding area under the graph 304 is displayed in a first colour (e.g. in blue). If the index 302 is between 21 and 40 (inclusive), the corresponding area under the graph 304 is displayed in a second colour (e.g. in dark green, shown as item 318 in FIG. 3). If the index 302 is between 41 and 60 (inclusive), the corresponding area under the graph 304 is displayed in a third colour (e.g. in light green). If the index 302 is between 61 and 80 (inclusive), the corresponding area under the graph 304 is displayed in a fourth colour (e.g. in orange, shown as item 316 in FIG. 3). If the index 302 is between 81 and 100 (inclusive), the corresponding area under the graph 304 is displayed in a fifth colour (e.g. in red). The recording interface 300 may include a similar graph generated based on the cortical state data, and/or composite cortical state data, and/or cortical input data, for example, a portion of the graph is generated for display in a colour corresponding to a predetermined range of values, where each predefined range is represented by a different colour.

Figure 4:
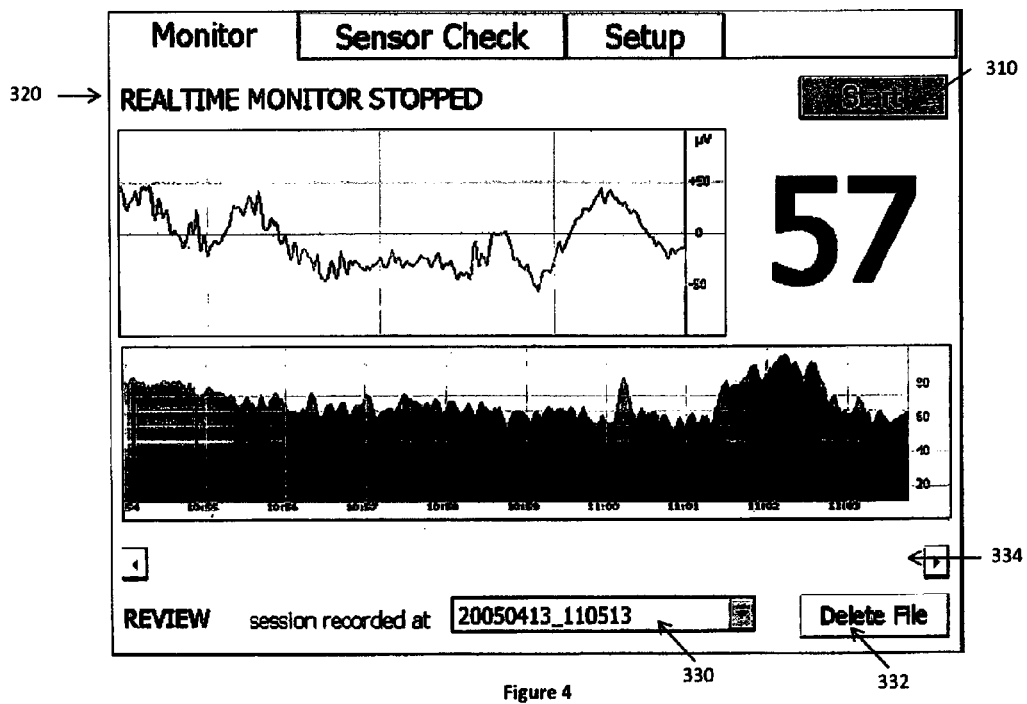
FIG. 4 is an EEG recording interface of the system in the review state.

FIG. 4 is the EEG recording interface 300 in the review state, i.e. when a user has operated the control button 310 to stop the system 100 from processing EEG signals. As shown in FIG. 4, the status field 320 displays a message indicating that processing has stopped. The interface 300 also includes a delete button 332 for deleting data associated with the recent EEG recording from memory 112, and a storage location field 330 (e.g. as a drop down menu) for a user to specify the storage location (e.g. file path and name) and/or parameters for exporting data associated with the recent EEG recording.

Figure 5:
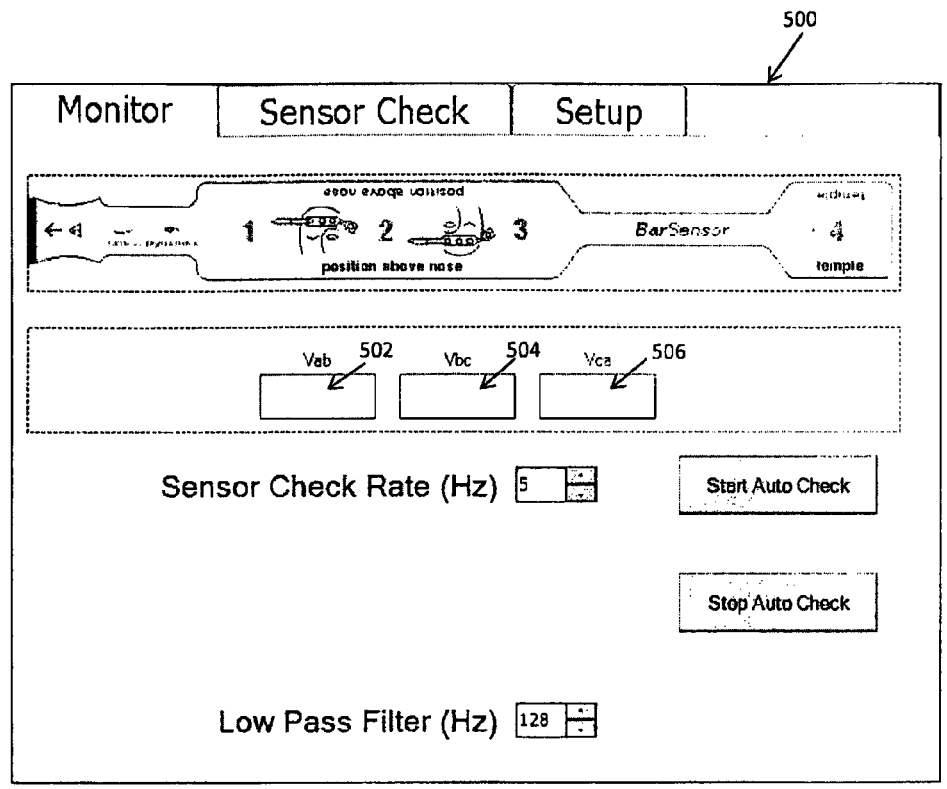
FIG. 5 is a sensor diagnostic interface of the system.

FIG. 5 is a sensor diagnostic interface 500 generated by the display module 114 when a user selects the sensor check tab 312. The diagnostic interface 500 enables a user to control a diagnostic process for verifying the operational status of the electrodes 102. The system 100, under the control of the diagnostic process, measures the impedance between each respective electrode and compares it to a reference value. The diagnostic interface 500 includes a flag 502, 504, 506 corresponding to each respective electrode, and a flag for a particular electrode is coloured if the electrode has impedance outside a range (e.g. if it is greater than 5-10 kOhms) necessary for accurate performance.

Figure 6:
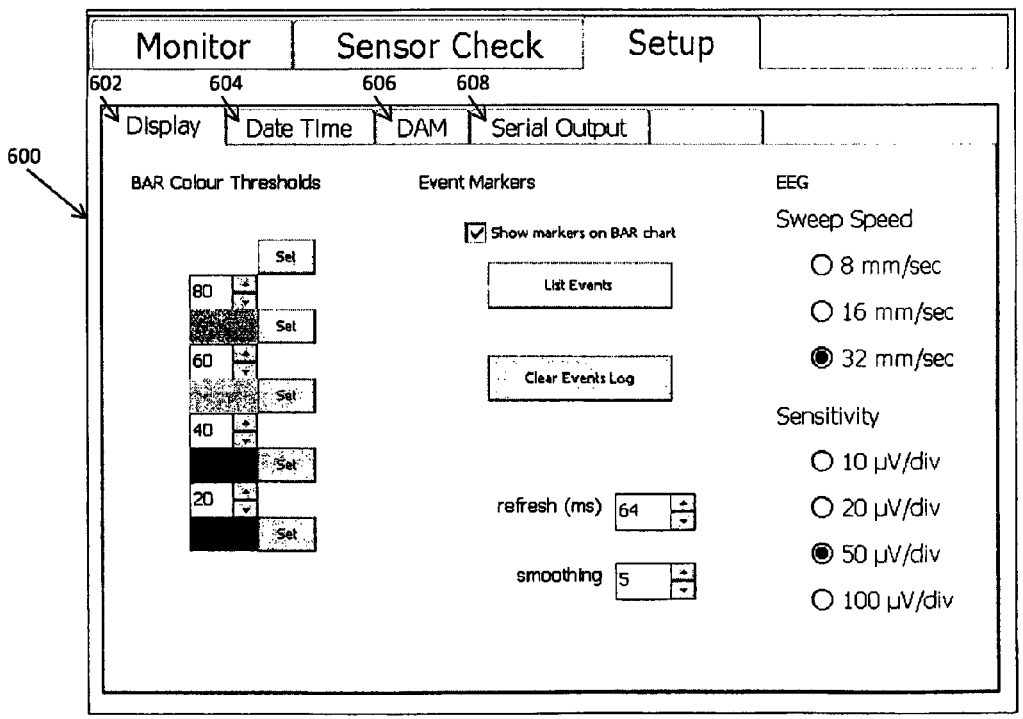
FIG. 6 is a setup interface of the system.

FIG. 6 is a setup interface generated by the display module 114 when a user selects the setup tab 314. The setup interface includes a display setup tab 602, date/time setup tab 604, system configuration tab 606, output setup tab 608 and a printer setup tab 610 for accessing user interfaces for configuring operating parameters of the EEG processing system 100. The display module 114 generates a display setup interface 600 when a user selects the display setup tab 602. The interface 600 includes fields for a user to select and/or configure each of the threshold brain function index levels/ranges and their corresponding colours; the events associated with each event marker button 324, 326, 328; the display refresh rate; display smoothing parameters; and the sweep speed and sensitivity (i.e. amplitude) of the EEG graph 306.

Figure 7:
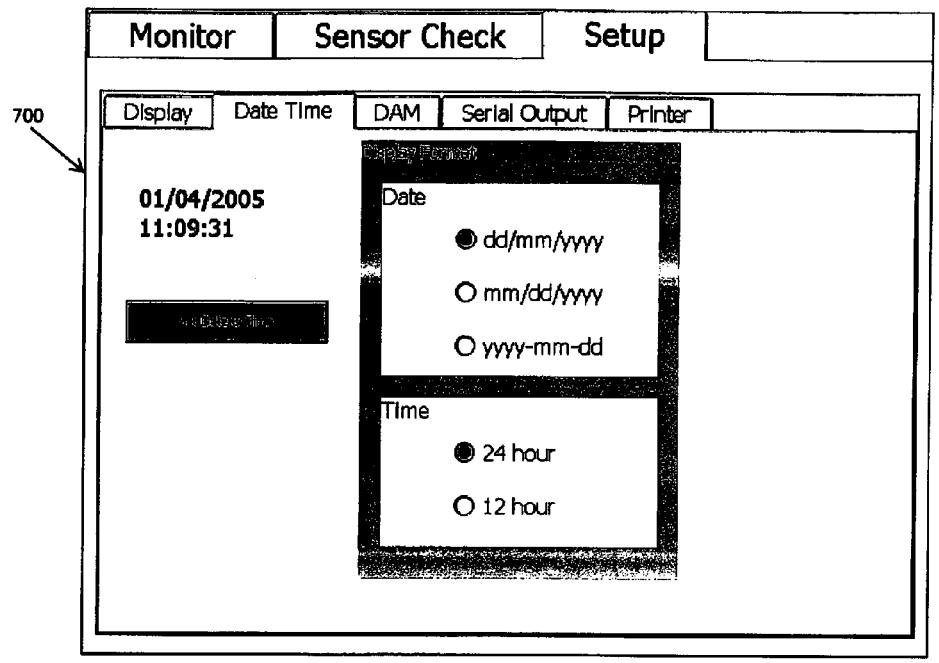
FIG. 7 is a date/time setup interface of the system.

FIG. 7 is a date/time setup interface 700 generated by the display module 114 when a user selects the date/time setup tab 604. The interface 700 includes fields for a user to select and/or configure the system clock date/time display format.

Figure 8:
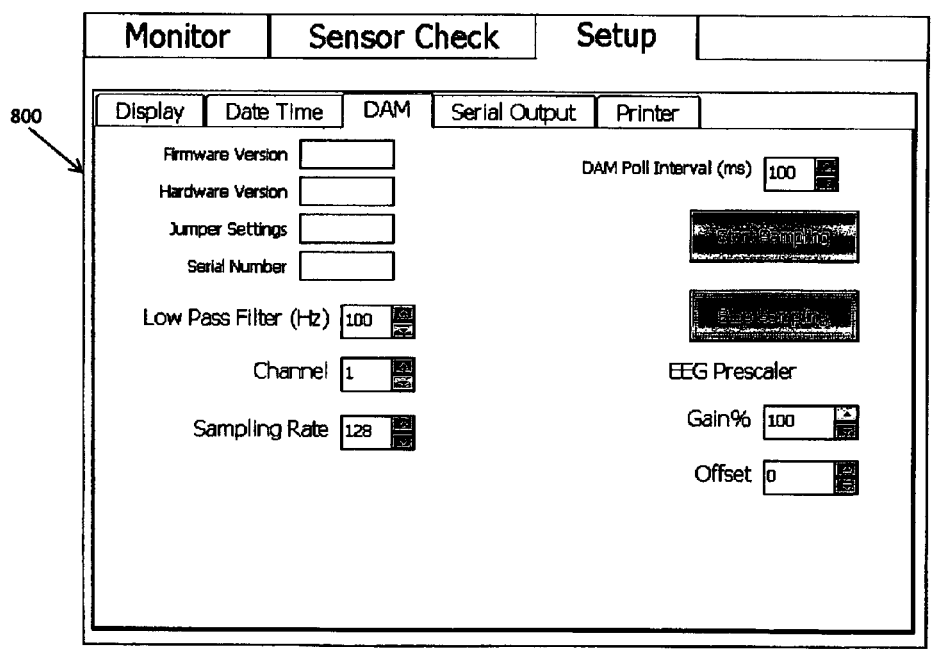
FIG. 8 is a system configuration interface of the system.

FIG. 8 is a system configuration interface 800 generated by the display module 114 when a user selects the system configuration tab 606. The interface 800 includes display fields for displaying the serial number, hardware version number, firmware version number, and jumper settings of the system 100. The interface 800 includes fields for a user to select and/or configure parameter values for the low pass filter, the channels for detecting EEG signals, the sampling rate, the polling interval (e.g. in milliseconds), and parameters for prescaling the EEG samples for display on the EEG graph 304.

Figure 9:
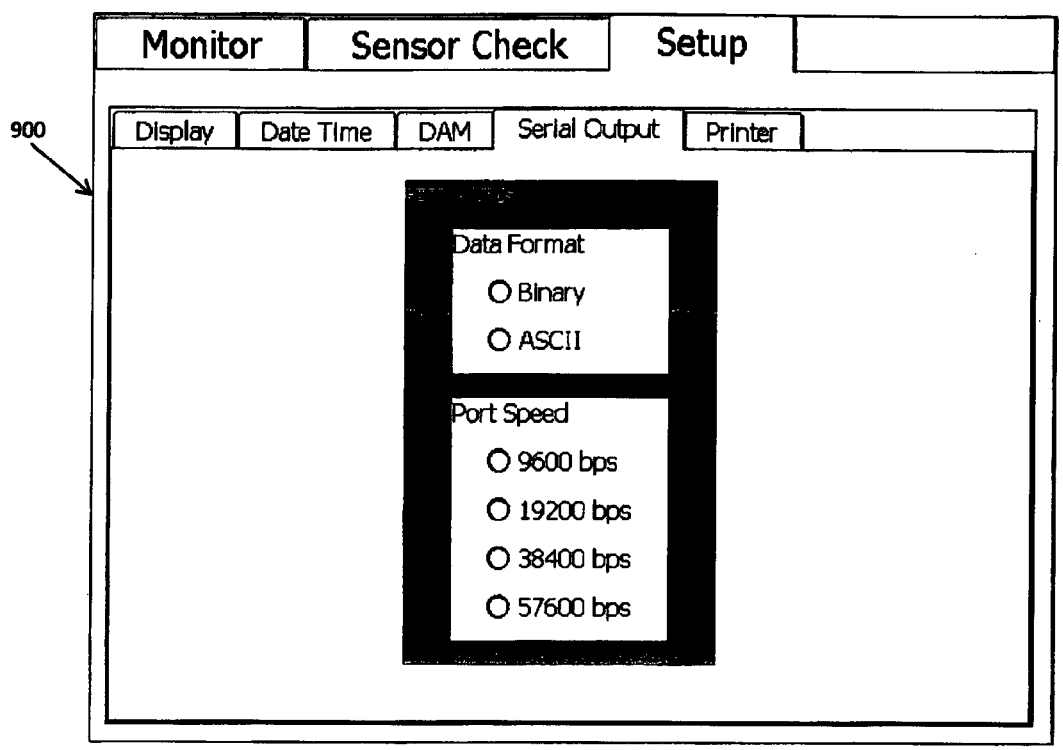
FIG. 9 is an output setup interface of the system.

FIG. 9 is an output setup interface 900 generated by the display module 114 when a user selects the output setup tab 608. The interface includes fields for a user to select and/or configure the type and/or format of the output data generated by the data export module 116, and the port speed (e.g. for a serial port) of the data export module 116. Output data generated by the data export module 116 is transferred to an output device 104a (e.g. a printer, disk drive, USB port, serial/parallel port, etc.). Output data generated by the data export module 116 may represent: i) a patient status report (e.g. including graphs, charts, a summary description of the patient's brain function status, and/or changes of this status over time); ii) a signal output representative of a recorded EEG signal; and/or iii) a data file including any of the features described above.

The display module 114 generates a printer setup interface when a user selects the printer setup tab 610, which includes user adjustable fields for selecting and configuring the type and/or format of the output data generated by the data export module 116 for an output device 104a (e.g. a printer).

The configuration module 120 of the EEG processing system 100 receives user input from the input device 118, and generates configuration data for controlling the operation of the brain function index calculation module 108 and the display processor module 114. The configuration data includes control signals, parameters and/or instructions that controls modules 108 and/or 114 to perform one or more of the following: i) select a processing option for processing the EEG samples; ii) define the degree of overlap between adjacent segments/windows; iii) configure module 108 to store the EEG samples and brain function data in memory 112: iv) define the display characteristics of user interfaces generated by the display module (e.g. including the layout of the interface displays, screen size, screen refresh rate, sweep speed and sensitivity of graphs displayed, brain function index threshold ranges and corresponding colours, smoothing settings, etc.) v) define date and time settings; vi) define event marker settings (e.g. including the number and type of events associated with each event marker button, and the colour associated with each type of event); vii) define date export settings (e.g. including the type, format and/or transmission speed of data output to be generated by the data export module 116); and/or viii) define, select or configure other operation parameters of the system 100 (such as the sensor check rate, and the band-pass filter range (Hz) for the filtering performed by modules 106 and 108).

The integrity testing module 110 continually evaluates the detected EEG signal from the electrodes 102 by comparing the signal against expected parameters (e.g. raw EEG RMS amplitude in the range 2 to 100 microvolts, and 90% of EEG power between 0 and 30 Hz) in order to determine the operational status of the electrodes 102.

An EEG signal detected from a subject can be analysed on the basis of a theoretical assumption that the EEG signal is the result of a filtered random process. As described in International Patent Publication WO 2004/064633, an EEG signal detected from a subject could be described mathematically as Equation 1:

$$H_e(\omega; q) = \frac{N(\omega; q)}{D(\omega; q)} P(\omega) \qquad \text{Equation 1}$$

where $H_e$ represents the EEG signal in the frequency domain, and P represents the input into the subject's cortex from other parts of the brain which can be used to assess the functional state of the cortex. N and D define polynomials in ω, the roots of which determine the dominant frequencies of the EEG signal. P(ω) is assumed to represent Gaussian white noise, and is therefore independent of the frequency ω (i.e. P(ω)=P₀ is a constant that is theoretically determined as being proportional to the magnitude of the subcortical input). In Equation 1, q represents a list of physiological parameters that theoretically determine the coefficients of the polynomials in ω for both the numerator N and denominator D.

The EEG signal for each respective segment/sample point can be expressed as a time invariant ARMA time series representation, and more advantageously, as a respective fixed order time invariant ARMA time series representation with an autoregressive order of 8 and a moving average order of 5. Equation 2 is a difference equation representing a (8,5) order ARMA representation for generating a representation of a portion of an EEG signal:

$$y[n] = -\sum_{k=1}^{8} a_k y[n-k] + \sum_{k=0}^{5} b_k u[n-k] \qquad \text{Equation 2}$$

where y[n] represents an ordinal sequence of sampled EEG signal values (i.e. y[n] is the n-th sequential sample), y[n−k] represents the k-th prior sampled value of y[n]; u[n−k] represents a Gaussian white noise process; and $a_k$ and $b_k$ is included in the coefficient data and respectively represent the AR (autoregressive) coefficients and MA (moving average) coefficients for a portion of an EEG signal corresponding to a segment. Estimates of the AR and MA coefficients can be generated in a number of ways, for example, using the ARMASA Matlab Toolbox application by P.M.T. Broersen of Delft University of Technology, or using any other ARMA modelling software package.

A time invariant ARMA representation of an EEG signal, as shown in Equation 2 can be re-written as a time varying ARMA time-series representation of an EEG signal as shown in Equation 3:

$$y[n] = -\sum_{k=1}^{8} a_k^{(n)} y[n-k] + \sum_{k=0}^{5} b_k^{(n)} u[n-k] \qquad \text{Equation 3}$$

The AR and MA coefficients for Equation 3, represented by $a_k^{(n)}$ and $b_k^{(n)}$ respectively, are expressed as a function of time (for time instant n). By denoting Equations 4 and 5:

$$\theta_n = (-a_1^{(n)}, \ldots, -a_8^{(n)}, b_1^{(n)}, \ldots, b_5^{(n)})^T \qquad \text{Equation 4}$$

$$\phi_n = (y_{n-1}, \ldots, y_{n-8}, u_{n-1}, \ldots, u_{n-5})^T \qquad \text{Equation 5}$$

Equation 3 can be re-written in state-space form as Equation 6:

$$y_n = \phi_n^T \theta_n + u_n \qquad \text{Equation 6}$$

where $\phi_n^T$ represents a regression vector, $\theta_n$ represents model parameters (or states) corresponding to those in Equation 4, and $u_n$ represents a Gaussian white noise process corresponding to u[n−k] in Equation 3. By assuming that the model parameters $\theta_n$ evolve as a random walk when no a priori information is available, $\theta_n$ can be estimated recursively from previous values of $\theta_n$ and $y_n$ according to the following general scheme shown in Equation 7:

$$\hat{\theta}_n = \hat{\theta}_{n-1} + K_n \epsilon_n \qquad \text{Equation 7}$$

where $K_n$ and $\epsilon_n$ represent the recursively determined filter gain and prediction error of the ARMA model estimated at the previous sample point of the EEG signal, respectively. A variety of methods are available to recursively generate estimates of the time varying AR and MA coefficients $\theta_n$. For example, it is possible to generate coefficient data based on a Kalman adaptive filtering method (e.g. as described in Tarvainen et al, *Estimation of non-stationary EEG with Kalman smoother approach: an application to event-related synchronization (ERS)*, IEEE Trans Biomed Eng, 2004, 51, pp. 516-524), or based on any other recursive processing method (e.g. a recursive processing method as described in Ljung L., *System Identification—Theory for the User*, Prentice Hall, Upper Saddle River, N.J. 2nd edition 1999), or using software (e.g. the functions associated with the MATLAB® System Identification Toolbox version 7.4), to generate optimal estimated values (e.g. in the mean square sense) for the model parameters in $\theta_n$ (expressed as $\hat{\theta}_n$).

Equations 2 and 3 can be rewritten in the z-domain notation, as shown in Equation 8:

$$Y(z) = \frac{\sum_{k=0}^{5} b_k z^{-k}}{\sum_{k=0}^{8} a_k z^{-k}} U(z) \qquad \text{Equation 8}$$

where Y(z) represents an ARMA representation of a portion of the EEG signal in the z-domain; U(z) represents a Gaussian white noise process in the z-domain; and the coefficients $a_k$ and $b_k$ respectively correspond to the AR and MA coefficients for the corresponding segment/sample point. In general, the estimation of ARMA coefficients involves defining $b_o$ and $a_o$ as unity.

The poles associated with the system described by Equation 8 correspond to the roots of the denominator in Equation 8. The poles data for each segment/sample point are generated based on Equation 9 using the coefficient data for the corresponding segment/sample point (where the poles are represented by p). There are 8 possible solutions (or poles) to Equation 9, not all of which are necessarily distinct.

$$\sum_{k=0}^{8} a_k p^{-k} = \sum_{k=0}^{8} a_k p^{8-k} = 0 \qquad \text{Equation 9}$$

The zeros associated with the system described by Equation 8 correspond to the roots of the numerator in Equation 8. The zeros data for each segment/sample point are generated based on Equation 10 using the coefficient data for the corresponding segment/sample point (where the zeros are represented by z). There are 5 possible solutions (or zeros) to Equation 10, not all of which are necessarily distinct.

$$\sum_{k=0}^{5} b_k z^{-k} = \sum_{k=0}^{5} b_k z^{5-k} = 0 \qquad \text{Equation 10}$$

The poles and zeros represented by the data generated based on Equations 9 and 10 are complex numbers. The poles and zeros for each respective segment/sample point can be plotted on a z-plane, where a change in the position of one or more of the poles and/or zeros, or a change in a mean position of the poles and/or zeros, represents a change in the functional state of the subject's brain. However, it is technically quite difficult to quantify the functional state of a brain based on the movement of one or more of the poles and/or zeros.

As described in International Patent Publication WO 2004/064633, it is expected that various pharmacological interventions result in the motion of a subset of the poles of Equation 8 when plotted in a complex plane (or z-plane). It is possible to quantify the motion of a subset of the poles by generating a value, designated as cortical state, representative of the mean motion of all of the poles represented by the data generated based on Equation 8. In particular, it is found that the mean real part of the pole motion is particularly sensitive to pharmacological manipulation/intervention to a brain.

The mean pole location $\bar{z}_p$ can be determined from the sum of the poles $\langle z_p \rangle$. For an ARMA model with an autoregressive order of 8, $\langle z_p \rangle$ can be calculated using Equation 11 where $z_{i,p}$ represents the i-th pole:

$$\langle z_p \rangle = \sum_{i=1}^{i=8} z_{i,p} \qquad \text{Equation 11}$$

Alternatively, as a consequence of the properties of polynomials, the sum of the poles $\langle z_p \rangle$ can be determined from the first AR coefficient generated based on Equation 2 (represented as $a_1$), i.e.

$$\langle z_p \rangle = -a_1 \qquad \text{Equation 12}$$

The mean pole location $\bar{z}_p$ can be determined by dividing $\langle z_p \rangle$ by the number of poles. For an ARMA model with an autoregressive order of 8, $\bar{z}_p$ is equal to $\langle z_p \rangle /8$. Because poles $z_{i,p}$, if complex, exist in complex conjugate pairs $\bar{z}_p$ will always be real.

As the mean pole location is to be scaled to form an appropriate index signifying cortical state (i.e. a numeric value that, for example, ranges from 0 to 100) it is not necessary to perform this division to represent the mean pole location. Instead, it is possible to determine the effect of changes in the mean pole location based on the value of $\langle z_p \rangle$ itself.

Because the mean pole will always be greater than or equal to −1 and less than or equal to 1 it can be appropriately scaled so that it extends over the interval 0 to 100. For instance the mean pole may be linearly scaled based on Equation 13 to give an index representative of cortical state:

$$\text{index} = c - m \langle z_p \rangle \qquad \text{Equation 13}$$

where c and m are constants chosen to ensure that index lies in some pre-defined range and $\langle z_p \rangle$ is used to represent the mean pole instead of $\bar{z}_p$. The mean pole may also be nonlinearly scaled to give an index representative of cortical state based on Equation 14:

$$\text{index} = \frac{d}{1 + e^{-a(\langle z_p \rangle - b)}} \qquad \text{Equation 14}$$

where a, b and d are constants chosen to ensure that the index lies in some pre-defined range and $\langle z_p \rangle$ represents the mean pole.

Cortical state data for each respective segment/sample point represented as an index number is generated based on either Equation 13 or Equation 14 using the mean pole data for the corresponding segment/sample point. Alternatively, the mean real pole data may be processed by a suitably defined and constructed discriminant function to produce a single scalar quantity representing cortical state. Such a discriminant function can be determined via stepwise discriminant analysis using for example the stepwise discriminant function analysis function/procedure of IBM SPSS Statistics (SPSS Inc. Chicago, USA) or a similar function widely available in any number of commercially available statistical software suites.

The cortical state data derived from the mean pole data for each respective segment/sample point is plotted as a graph to show changes in the responsive state of the cortex as a function of time or relative to the corresponding segment/sample point number. Cortical state is expected to either increase or decrease in response to therapeutic intervention or disease. Alternatively, other parameters may be derived from the AR and MA coefficients to represent changes in the responsive state of the cortex. For example, it is possible to quantify the motion of the zeros of Equation 8 using the mean zero location in a manner similar to using the mean pole location to quantify pole motion. However, due to the underlying physiological theory (as described in International Patent Publication WO 2004/064633) the zeros are not expected to move independently of the poles and therefore monitoring mean zero motion is expected to have limited utility in the assessment of the brain function of a subject.

As the polynomials of both the numerator and denominator of Equation 1 are theoretically dependent on a range of physiological parameters, q, a measure that quantifies the motion of the zeros of Equation 8 in conjunction with the motion of the poles is a pertinent alternative measure of the responsive state of the cortex. However, it is quite difficult to combine the pole and zero data into a single scalar measure that is both meaningful and physiologically relevant. One approach is to exploit the relationship between ARMA and AR time series models.

A theorem by Kolmogorov (detailed in Kolmogorov A N, *Interpolation and Extrapolation von Stationären Zufälligen Folgen*, Bull. Acad. Sci. USSR Ser. Math, Vol. 5, 1941, pp. 3-14 and discussed in Kay S, *Modern Spectral Estimation—Theory and Application*, Prentice Hall, Englewood Cliffs, N.J. 1988) states that any ARMA model can be equivalently expressed as an AR model of infinite order. The poles of the infinite order AR model are positioned according to locations of the poles and zeros of the original ARMA model. Subsequently, the motion of the poles of the infinite AR model can be used to measure the motion of the poles and zeros of the ARMA model.

The coefficients of the infinite AR model can be determined from the ARMA model coefficients using a recursive difference equation (see for example Kay S, *Modern Spectral Estimation—Theory and Application*, Prentice Hall, Englewood Cliffs, N.J. 1988):

$$c_n = -\sum_{k=1}^{q} b_k c_{n-k} + \sum_{k=0}^{p} a_k \delta_{n-k}; \quad n \geq 0 \qquad \text{Equation 15}$$

where $c_n$ are the coefficients of the infinite order AR model, $a_k$ and $b_k$ respectively correspond to the AR and MA coefficients of the ARMA model, p and q are the respective orders of the AR and MA parts of the ARMA model and $\delta_{n-k}$ is a Dirac delta function. The values of $c_{n-k}$ are set equal to zero for n−k<0.

As a consequence of the properties of polynomials, the first AR coefficient, $c_1$, of the infinite order AR model, corresponds to the negative of the sum of the poles and can therefore be used to provide a scalar measure of the corresponding ARMA filter structure. Assuming $a_0$ and $b_0$ are unity, $c_0$ equates to unity and $c_1$ can be calculated by reducing Equation 15 to:

$$c_1 = a_1 - b_1 \qquad \text{Equation 16}$$

The resulting measure, calculated from the first AR and MA coefficient from the estimated ARMA process, is denoted the composite cortical state. It can be used to represent the responsive state of the cortex and provides a complementary, but distinct, measure of such responsiveness compared to cortical state. Alternatively, as for the calculation of the mean pole location of a fixed order AR or ARMA model, there is another method for calculating the composite cortical state given by $c_1$. Because based on Equations 9-12 the coefficients $a_1$ and $b_1$ can be expressed as follows:

$$a_1 = -\sum_{i=1}^{i=p} z_{i,p} \equiv -\langle z_p \rangle \qquad \text{Equation 17}$$

and $$b_1 = -\sum_{i=1}^{i=q} z_{i,z} \equiv -\langle z_z \rangle \qquad \text{Equation 18}$$

where $z_{i,p}$ is the i-th pole, $z_{i,z}$ is the i-th zero of the AR order p and MA order q ARMA model, and $\langle z_z \rangle$ is the sum of the zeros, the composite cortical state $c_1$ can also be calculated as the negative of the difference of the sum of the poles and zeros of this (p,q) ARMA model $$c_1 = -\sum_{i=1}^{i=q} z_{i,p} + \sum_{i=1}^{i=q} z_{i,z} \equiv -\langle z_p \rangle + \langle z_z \rangle \qquad \text{Equation 19}$$

For an AR model of infinite order, dividing the negative of $c_1$ by the number of poles (which is infinite) to obtain the mean pole location will always result in a mean pole location at the origin of the z-plane. As such this average will be unable to provide a meaningful scalar measure of the ARMA filter state. However, as $a_1$ (sum of the poles) and $b_1$ (sum of the zeros) are bounded by the order of the ARMA model, the sum of the poles of the infinite AR model, $c_1$, is also bounded. For the case of an ARMA model of AR order 8 and MA order 5, $a_1$ and $b_1$ are bounded to be within plus and minus 8 and plus and minus 5 respectively and $c_1$ is bounded to the range between plus and minus 13. This allows the composite cortical state measure to be scaled so that it will always be greater than or equal to −1 and less than or equal to 1 by dividing $c_1$ by 13.

The composite cortical state can also be scaled to form an index (i.e. a numeric value that, for example, ranges from 0 to 100) using Equations 13 and 14 with the sum of the poles of the infinite order AR model, $\langle z_p \rangle$, which is obtained from $c_1$. Alternatively, the discriminant function referred to above can be used to scale composite cortical state to form an appropriate index. The composite cortical state data for each respective segment/sample point can be plotted as a graph to show changes in the responsive state of the cortex as a function of time or relative to the corresponding segment/sample point number. Composite cortical state is expected to either increase or decrease in response to therapeutic intervention or disease.

A similar measure can be obtained by using a corollary of the Wold decomposition theorem (detailed in Wold H, *A Study in the Analysis of Stationary Time Series*, Almqvist & Wiksell, Stockholm, 1954 and discussed in Kay S, *Modern Spectral Estimation—Theory and Application*, Prentice Hall, Englewood Cliffs, N.J. 1988) that any ARMA model can be equivalently expressed as a MA model of infinite order. The motion of the zeros of the infinite MA model can be used as a measure of the motion of the poles and zeros of the ARMA model in the same manner as the poles of the infinite AR model described above. However this approach provides no meaningful alternative or greater advantage to the method already disclosed above as, by a consequence of the relationships between time series models, the sum of the zeros of an infinite MA representation equates to the negative of the sum of the poles of an infinite AR representation, i.e. the sum of the zeros of the infinite order MA model equals $-c_1$ where $c_1$ is defined as in Equation 16. Thus by defining a scalar measure of the estimated ARMA filter in terms of the sum of the poles of infinite order AR or the sum of the zeros of an infinite order MA model leads to the same essential measure. In other words, the two approaches for calculation of the composite cortical state give equivalent results.

The theoretically derived transfer function shown in Equation 1 can be rewritten in a factored canonical form as Equation 20:

$$H_e(\omega; q) = \frac{g(q) \prod_{k=1}^{k=5} [i\omega - z_k'(q)]}{\prod_{k=1}^{k=8} [i\omega - p_k'(q)]} P(\omega) \quad \text{Equation 20}$$

where $P(\omega)$ represents the level of cortical input to the brain. Due to the expected temporal complexity of cortical input in the actual cortex, such input is assumed to be indistinguishable from, and representative of a Gaussian random (white noise) process. In Equation 20, values for each of the 8 poles (represented by $p_k'$) and 5 zeros (represented by $z_k'$) are determined based on a number of physiological parameters (represented by q). The values of $z_k'$ for Equation 20 are generated based on Equation 21 using the zeros data generated based on Equation 10. The values of $p_k'$ for Equation 20 are generated based on Equation 21 using the poles data generated based on Equation 9.

$$z_k' = f_s \ln|z_k| + f_s Arg(z_k)/2\pi \quad \text{Equation 21}$$

$$p_k' = f_s \ln|p_k| + f_s Arg(p_k)/2\pi \quad \text{Equation 22}$$

where $f_s$ is the EEG sampling (digitisation) frequency. In Equation 20, $g(q)$ represents a gain factor that depends explicitly on one or more of the parameters represented by q. In theory, it is expected that the value of $g(q)$ for a subject remains generally unchanged both before and during the application of an intervention to the subject (e.g. an anaesthetic agent) which affects the functional state of the cortex. Accordingly, the value of $g(q)$ is assumed to be a constant. The product $g(q)P(\omega)$ can be used to estimate the level of cortical input to the subject's brain, and since $g(q)$ is assumed to be a constant, it is expected that any changes in the value of $g(q)P(\omega)$ are caused by changes in $P(\omega)$.

The EEG processing system 100 generates, based on Equation 23, cortical input data for representing the cortical neuronal input received by the subject's brain at a particular point in time. Equation 23 assumes that $P(\omega)$ represents Gaussian white noise:

$$g(q)P(\omega) = \frac{\langle \tilde{Y}(t) \rangle}{\langle Y(t) \rangle} \quad \text{Equation 23}$$

where $\langle \tilde{Y}(t) \rangle$ represents an average signal amplitude of a portion of an EEG signal (e.g. of a selected segment of an EEG signal); and $\langle Y(t) \rangle$ represents an ARMA gain value for the corresponding portion of the EEG signal. The value of $\langle \tilde{Y}(t) \rangle$ can be determined as the root mean square (RMS) of the amplitude of the EEG signal for selected times using a fixed length window, if a time invariant ARMA representation is used, or for every sample point by using a fixed length sliding window, if a time variant ARMA representation is used. The ARMA gain value $\langle Y(t) \rangle$ can be determined as the RMS of the amplitude of a signal representation of the EEG signal for the selected segment/sample point.

The AR and MA coefficients for a selected segment is generated based on a time-invariant ARMA representation (i.e. based on Equation 2), so a signal representation of the EEG signal for that segment is generated based on Equation 2. The signal representation represents a sequence of values generated based on Equation 2 (i.e. y[n] in Equation 2), where the output of Equation 2 is generated based on the estimated AR and MA coefficients for the selected segment, when driven by a normalised white noise input (i.e. where u[n−k] represents random values determined by a zero mean unit variance Gaussian random process).

The AR and MA coefficients for a selected sample point are generated based on a time-varying ARMA representation (i.e. based on Equation 3), a signal representation of the EEG signal for that sample point is generated based on Equation 3. The signal representation represents a sequence of values (i.e. y[n] in Equation 3), where the output of Equation 3 is generated based on the AR and MA coefficients for the selected sample point, when driven by a normalised white noise input (i.e. where u[n−k] represents random values determined by a zero mean unit variance Gaussian random process).

ARMA gain can be generated in a number of ways, for example, using the arma2cor function of the ARMASA Matlab Toolbox application by P.M.T. Broersen of Delft University of Technology, or using any other ARMA modelling software package.

Equations 2 and 3 represent a fixed order (8,5) ARMA representation of a portion of an EEG signal. Although an ARMA representation having an autoregressive order of 8 and moving average order of 5 is expected to give the best results, other AR and MA orders can be selected.

Theoretically, the gain factor, g, depends on the parameters, q, according to Equation 24:

$$g \cong \frac{\exp(1)\psi_e[h_e^*(q)]\gamma_e}{\tau_e} \quad \text{Equation 24}$$

and thus cortical input, $P(\omega)$, can be estimated using Equation 25:

$$P(\omega) \cong \frac{\tau_e \langle \tilde{Y}(t) \rangle}{\exp(1)\psi_e[h_e^*(q)]\gamma_e \langle Y(t) \rangle} \quad \text{Equation 25}$$

where, in Equations 24 and 25, $\psi_e[h_e^*(q)]$ represents the efficacy of excitation in cortex (and which is proportional to the transmembrane driving force for excitatory activity at rest), $\gamma_e$ represents the corresponding rate constant for excitation, and $\tau_e$ represents the effective passive membrane time constant. In mean field modelling, the respective values for $\psi_e[h_e^*(q)]$, $\gamma_e$ and $\tau_e$ during intervention are not expected to be significantly perturbed from their undisturbed values. The product g(q)P(ω) determined using Equation 23 is denoted the cortical input. Cortical input, together with the poles and zeros obtained from the coefficients $a_k$ and $b_k$ in Equations 2 or 3, represents a more comprehensive linear characterisation of the dynamics of the EEG signal detected from the subject, than using the ARMA coefficients alone.

Thus, armed with knowledge about how a particular pharmaceutical agent affects single neuronal physiological properties, of which there is extensive information, the technique disclosed herein can be used to determine variations in input to the brain that are affected by said pharmaceutical agents. This is of particular relevance when it is considered that a variety of pharmaceutical agents known to affect brain function have sites and targets of action that are distributed throughout the central nervous system.

For example, nitrous oxide is both a hypnotic and analgesic agent and is known to affect sites cortically and subcortically (e.g. as discussed in Hopkins P M, *Nitrous oxide: a unique drug of continuing importance for anaesthesia*, Best Pract Res Clin Anaesthesiol., 2005, Sep., 19(3), pp. 381-9; and Rudolph U & Antkowiak B., *Molecular and neuronal substrates for general anaesthetics.*, Nat Rev Neurosci., 2004, Sep., 5(9), pp. 709-20). Being able to non-invasively quantify both the levels of hypnosis and analgesia is of great clinical utility, as separate measures have important implications in terms of subsequent and ongoing clinical management and clinical outcome. For example, detecting adequate analgesia is important for achieving physiological (autonomic) stability during surgical procedures, and helps improve postoperative clinical outcomes. Quantifying the magnitude of subcortical input may provide one way of assessing the level of analgesia by monitoring the degree to which peripherally derived sensory information reaches cortex.

The derived measures of cortical input, cortical state and composite cortical state may be displayed individually, or synthesised into a single index representing the functional state of the subject's brain. Numerous methods are available to combine these measures into a single number. For example, an index may be calculated as the length of a vector projecting into a three dimensional space defined by the measures of cortical input, cortical state and composite cortical state such that:

$$\text{index} = \sqrt{(\alpha CI)^2 + (\beta CS)^2 + (\gamma CS_c)^2} \qquad \text{Equation 26}$$

where CI represents cortical input, CS corresponds to cortical state. $CS_c$ is composite cortical state and $\alpha$, $\beta$ and $\gamma$ represent appropriate scaling factors or functions. The resulting index may then be scaled to a predefined range (e.g. from 0 to 100) using appropriate variations of Equations 13 and 14. i.e.

$$\text{scaled index} = m \times \text{index} - c \qquad \text{Equation 27}$$

where c and m are constants chosen to ensure that index lies in some pre-defined range and index is as defined in Equation 26. The index as defined in Equation 26 may also be nonlinearly scaled to give the following scaled index:

$$\text{scaled index} = \frac{d}{1 + e^{-a \, \text{index} - b}} \qquad \text{Equation 28}$$

where a, b and d are constants chosen to ensure that the scaled index lies within a predefined range.

Alternatively, the cortical input, cortical state and composite cortical state data and other measures that can be extracted from the ARMA models or EEG data may be processed by the discriminant function referred to above to produce a single scalar quantity representing the functional state of a brain.

Figure 2:
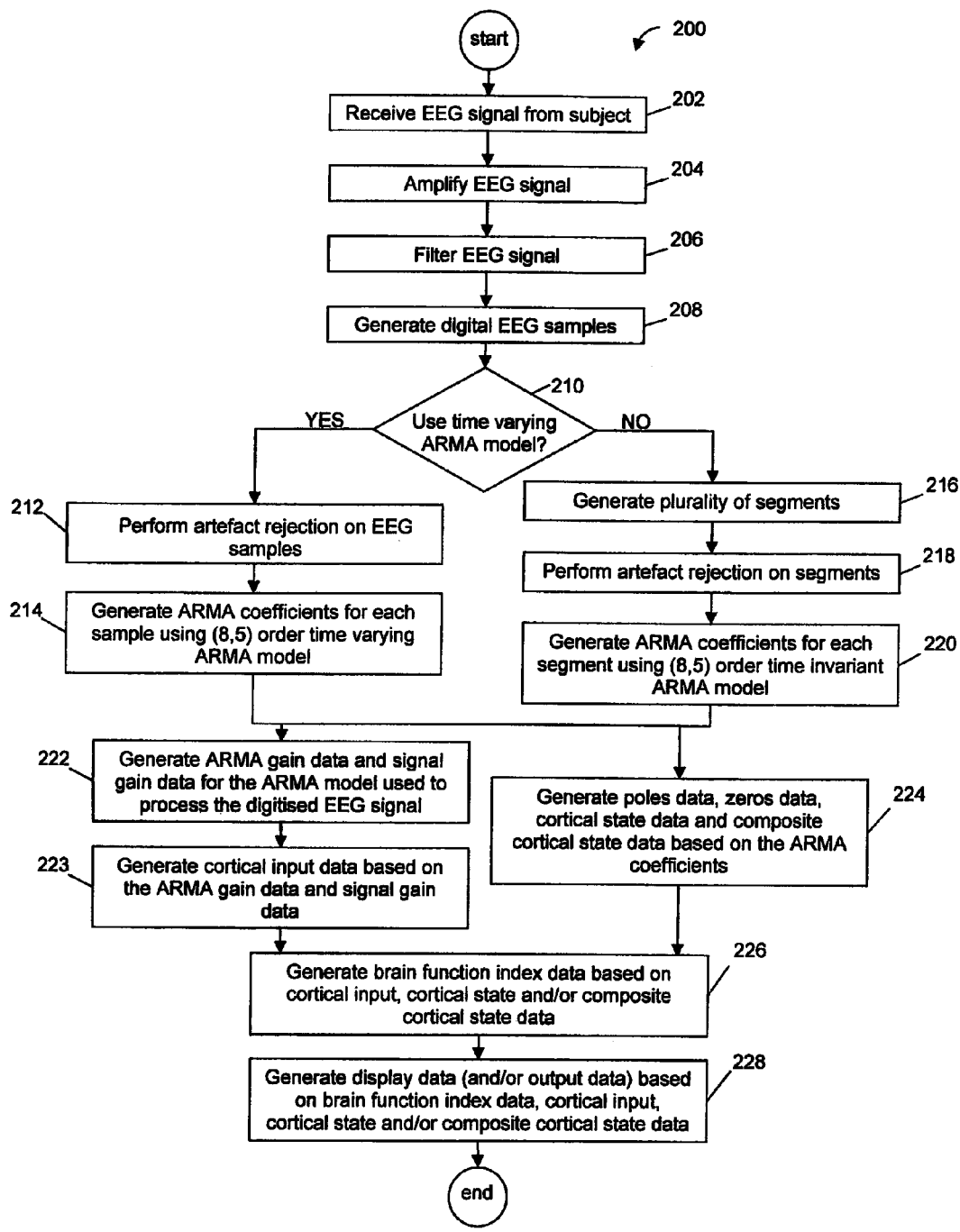
FIG. 2 is a flow diagram of the steps performed under the control of the system.

FIG. 2 is a flow diagram of an EEG analysis process 200 performed by the EEG processing system 100. Process 200 begins at step 202 with the signal processing module 106 receiving an EEG signal from the subject via the electrodes 102. At step 204, module 106 amplifies the EEG signal. At step 206, module 106 filters the EEG signal using a band-pass filtered to remove low frequency artefact, EMG components and main artefacts (generally arising between 0 Hz to 50-60 Hz), as well as other sources of external noise. At step 208, module 106 converts the EEG signal into digital EEG samples.

Step 210 decides how to process the EEG samples based on the user's selection. If the user selects a processing option for analysing the samples substantially in real-time, step 210 proceeds to step 212. Otherwise, a default processing option is selected and step 210 proceeds to step 216.

The brain function index calculation module 108 performs steps 212 and 214 in respect of each new sample point generated by the module 108. At step 212, module 108 performs additional artefact rejection and signal preprocessing on the EEG samples, including further removal of periodic 0 Hz to 50-60 Hz interference from the samples, which is known to compromise the subsequent estimation of AR and MA coefficients.

At step 214, module 108 generates coefficient data for each sample point representing the AR and MA coefficients for a time varying ARMA representation of the EEG signal (e.g. based on an (8,5) order ARMA representation) for each sampled EEG value obtained by digitisation. For example, at step 214, module 108 generates the AR and MA coefficients directly from the EEG samples using a Kalman adaptive filtering method. In step 214, the coefficient data represents the optimal values of the AR and MA coefficients as described above. Step 214 then proceeds to step 222 and step 224, which are performed in parallel to each other. The time varying coefficient data can be generated using software, such as the functions associated with the MATLAB® System Identification Toolbox version 7.4.

At step 216, module 108 generates a plurality of segments, each representing a portion of the digital EEG signal for the same duration. For example, each segment may represent a 2-second sample of the EEG signal and may overlap with a portion of an adjacent segment. At step 218, module 108 performs additional signal pre-processing including filtering each segment to remove additional artefacts from the signal, that includes removing periodic 0 Hz to 50-60 Hz interference which is known to compromise the subsequent estimation of AR and MA coefficients. At step 220, module 108 generates coefficient data based on the respective time invariant ARMA representation of the EEG signal (e.g. based on an (8,5) order ARMA representation) for each segment. Estimated of the AR and MA coefficients for each fixed length segment can be generated in a number of ways, for example, using the ARMASA Matlab Toolbox application by P.M.T. Broersen of Delft University of technology, or using any other ARMA modelling software package. Step 220 then proceeds to step 222 and step 224.

At step 222, module 108 generates, for each segment/sample point, ARMA gain data representing an ARMA gain value (i.e. ⟨Y(t)⟩ in Equation 23) based on the corresponding ARMA representation used in step 214 or 220 for generating the coefficient data for the corresponding segment/sample point. This involves applying the estimated AR and MA coefficients to the corresponding ARMA representation (i.e. Equation 2 or Equation 10), and generating a signal representation (represented by y[n]) by driving the corresponding ARMA representation with a normalised white noise input (represented by u[n−k]).

At step 222, module 108 also generates, for each segment/sample point, signal gain data representing a signal gain value (i.e. $\langle \tilde{Y}(t) \rangle$ in Equation 23) based on the EEG samples for the corresponding segment, in the case where a time-invariant ARMA representation is used (at steps 216, 218, 220), or for a range of EEG sample values in the case where a time varying ARMA presentation is used (at steps 212 and 214). The value of $(\langle \tilde{Y}(t) \rangle$ for each sample point is generated based on an appropriate portion of the detected EEG signal centred on the time at which the coefficient data for the corresponding sample point was generated, or generated based on an appropriately constructed average of the sampled EEG signal including and prior to the current sample point. Alternatively, a value of $\langle \tilde{Y}(t) \rangle$ is generated based on each respective segment generated by module 108 at step 216.

At step 223, module 108 then generates, for each segment/sample point, cortical input data representing the value of the product $g(q)P(\omega)$ according to Equation 23 based on the corresponding ARMA gain data and signal gain data. Changes in the value of the $g(q)P(\omega)$ represents changes in the magnitude of the subcortical input (represented by $P(\omega)$).

Step 224 generates poles data and zeros data based on Equations 9 and 10, and then module 108 generates cortical state data based on Equation 12 and composite cortical state data based on Equation 16 for each respective segment/sample point.

Steps 223 and 224 proceed to step 226, where module 108 generates brain function index data based on cortical input data, cortical state data and/or composite cortical state data representing a scaled numeric representation of brain function for the corresponding segment/sample point. For example brain function index data may be derived from combining cortical input state data, cortical state data and composite cortical state data according to Equation 26. This brain function data may then be scaled, based on using either Equation 27 or 28, to lie within a predefined range. This scaled brain function index is then sent to the display module 114 where it can be displayed in a variety of formats that include a single index value 302 and/or as a graph of sequential values 304 defined over a selected interval of time up to and including the present moment.

At step 228, the display module 114 generates display data representing user interfaces based on the brain function data (e.g. using the poles data, zeros data, cortical input data, cortical state data, composite cortical state data and/or brain function index data), and preferably including a representation of the EEG samples, to represent functional state of the subject's brain and/or level of subcortical activity in the subject's brain. Step 228 also controls the data export module to generate output data including data representative of the EEG samples, brain function data, raw and/or scaled cortical input, cortical state and/or composite cortical state data. Process 200 ends after step 228.

Changes in the value represented by the cortical state data and/or composite cortical state data represent changes in the functional state of the subject's brain (i.e. how the brain responds to cortical input). Changes in the value represented by the cortical input data represent changes in value of the product $g(q)P(\omega)$ and thus the level of brain cortical input. An advantage provided by the ARMA gain, and hence a measure of subcortical input, is to enhance the physiological specificity (and hence clinical utility) of the determination of the subject's brain function.

Many modifications will be apparent to those skilled in the art without departing from the scope of the present invention as herein described with reference to the accompanying drawings.

The reference to any prior art in this specification is not, and should not be taken as, an acknowledgment or any form of suggestion that that prior art forms part of the common general knowledge in Australia.

The invention claimed is:

1. A method of displaying the activity of a brain, the method including the steps of:
   (i) obtaining an electroencephalogram (EEG) signal from the brain using a plurality of electrodes and digitizing means; and using computing means for:
   (ii) segmenting said EEG signal into either contiguous or overlapping segments comprised of a sequential number of samples of said EEG signal;
   (iii) representing said EEG segments as a fixed order autoregressive moving average (ARMA) signal representation with an autoregressive order between 8 and 13 and a moving average order between 5 and 11;
   (iv) rewriting in z-domain notation said fixed order ARMA signal representation to obtain a z-domain representation;
   (v) generating autoregressive (AR) coefficient data and moving average (MA) coefficient data for said segments of said EEG signal for said fixed order ARMA signal representation;
   (vi) determining the poles and zeros of said z-domain representation for said segments of said EEG signal by substituting said coefficient data for said segments of said EEG signal into said z-domain representation;
   (vii) calculating the sum of the number of poles determined in step (vi);
   (viii) calculating the sum of the number of zeros determined in step (vi);
   (ix) representing said ARMA signal representation as an infinite order autoregressive (AR) model in z-domain notation;
   (x) determining autoregressive coefficient data for said infinite AR model from the AR and MA coefficient data generated in step (v) of said fixed order ARMA representation;
   (xi) determining the sum of the poles for said infinite order AR model for said segments of said EEG signal as either:
      (a) the first autoregressive coefficient of said infinite order AR model; or
      (b) the difference of the sum of poles and the sum of zeros as determined respectively in steps (vii) and (viii);
   (xii) determining an index value representing the activity of the brain for said segments of said EEG signal by applying a discriminating function to the sum of the poles of said infinite AR model for said segments of said EEG signal as determined in step (xi); and
   (xiii) displaying said index value on display means.

2. The method of claim 1 including the step of providing the user of the method an option to select a time varying or time invariant ARMA signal representation in step (iii).

3. The method of claim 2 including the steps of:
   (xiv) selecting a fixed order time invariant ARMA signal representation of autoregressive order 8 and moving average order of 5;

$$y[n] = -\sum_{k=1}^{8} a_k y[n-k] + \sum_{k=0}^{5} b_k u[n-k]$$

where y[n] represents an ordinal sequence of samples of said EEG signal, y[n−k] represents the k-th prior sampled value of y[n]; u[n−k] represents a Gaussian white noise process; and $a_k$ and $b_k$ represent the estimated autoregressive AR and moving average MA coefficient data determined in step (v) respectively for a said segment of said EEG signal (xv) estimating the autoregressive AR coefficients $a_1$-$a_8$ and moving average MA coefficients $b_0$-$b_5$ for the fixed order ARMA signal representation of the equation of step (xiv) for one or more said EEG segments;

(xvi) performing step (iv) on the equation of step (xiv) such that the z-domain representation is a z-domain equation;

$$Y(z) = \frac{\sum_{k=0}^{5} b_k z^{-k}}{\sum_{k=0}^{8} a_k z^{-k}} U(z)$$

(xvii) substituting estimated autoregressive AR and moving average MA coefficients into the z-domain equation of step (xvi);

(xviii) performing step (vi) on the z-domain equation of step (xvi) using the equations;

$$\sum_{k=0}^{8} a_k p^{-k} = \sum_{k=0}^{8} a_k p^{8-k} = 0$$

$$\sum_{k=0}^{5} b_k z^{-k} = \sum_{k=0}^{5} b_k z^{5-k} = 0$$

wherein there are 8 poles each represented by the symbol p and wherein there are 5 zeros represented by the symbol z; and (xix) performing step (xi) using either;

$$(a)\ c_1 = -\sum_{i=1}^{i=8} z_{i,p} + \sum_{i=1}^{i=5} z_{i,z} \equiv -\langle z_p \rangle + \langle z_z \rangle;\ \text{or}$$

$(b)\ c_1 = a_1 - b_1$ wherein $z_{i,p}$ is the i-th pole, $z_{i,z}$ is the i-th zero and $a_1$ and $b_1$ are the first autoregressive and first moving average coefficient respectively of said time invariant ARMA signal representation and $c_1$ is the first coefficient of the infinite order AR model.

4. The method of claim 3 including the steps of:

(xx) recursively estimating the autoregressive coefficients $a_1$-$a_8$ and moving average coefficients $b_0$-$b_5$ for each time instant n as $a_1^{(n)}$-$a_8^{(n)}$ and $b_0^{(n)}$-$b_5^{(n)}$ respectively so that the following fixed order time-varying ARMA representation will have been selected;

$$y[n] = -\sum_{k=1}^{8} a_k^{(n)} y[n-k] + \sum_{k=0}^{5} b_k^{(n)} u[n-k];\ \text{and}$$

(xxi) calculating step (xix)(b) using the equation $c_1^{(n)} = a_1^{(n)} - b_1^{(n)}$ wherein $a_1^{(n)}$ and $b_1^{(n)}$ are the first autoregressive and moving average coefficient respectively of said time varying ARMA representation of autoregressive order 8 and moving average order of 5 at time instant n.

5. The method of claim 1 wherein the index value is a number in the range 0-100.

6. The method of claim 5 wherein the index value is determined using the equation:

index=$c-m\langle z_p \rangle$ wherein c and m are constants selected such that the index value lies within said range and $\langle z_p \rangle$ is the sum of the poles of said infinite order AR model.

7. The method of claim 5 wherein the index value is determined using the equation:

$$\text{index} = \frac{100}{1 + e^{-a(\langle z_p \rangle - b)}}$$

wherein a and b are constants selected such the index value lies within said range and $\langle z_p \rangle$ is the sum of the poles of said infinite order AR model.

8. The method of claim 1 wherein the index value is determined using a scaling function determined by applying discriminant analysis to the sum of the poles of said infinite order AR model as determined in step (xi).

9. The method of claim 1 wherein the index value is determined by combining the sum of the poles of said infinite order AR model with measures of cortical state and cortical input, that are also derived from the ARMA model and EEG data, using a function determined by applying discriminant analysis.

10. The method of claim 1 wherein step (xiii) includes the step of displaying said index value in graphical form.

11. The method of claim 1 wherein step (xiii) includes the step of displaying said index value in colours corresponding to different predetermined ranges of values of said index value, wherein each predetermined range is represented by a different colour.

12. A system for displaying the activity of a brain of a subject, the system including:
a plurality of electrodes for picking up electroencephalogram signals from the brain of the subject;
digitising means for converting the EEG signals to a digitised EEG data signal; and
computing means for:
(i) segmenting said EEG signal into either contiguous or overlapping segments comprised of a sequential number of samples of said EEG signal;
(ii) representing said EEG segments as a fixed order autoregressive moving average (ARMA) signal representation with an autoregressive order between 8 and 13 and a moving average order between 5 and 11;
(iii) rewriting in z-domain notation said fixed order ARMA signal representation to obtain a z-domain representation;
(iv) generating autoregressive (AR) coefficient data and moving average (MA) coefficient data for said segments of said EEG signal for said fixed order ARMA signal representation;

(v) determining the poles and zeros of said z-domain representation for said segments of said EEG signal by substituting said coefficient data for said segments of said EEG signal into said z-domain representation;
(vi) calculating the sum of the number of poles determined in step (v);
(vii) calculating the sum of the number of zeros determined in step (v);
(viii) representing said ARMA signal representation as an infinite order autoregressive (AR) model in z-domain notation;
(ix) determining autoregressive coefficient data for said infinite AR model from the AR and MA coefficient data generated in step (iv) of said fixed order ARMA representation;
(x) determining the sum of the poles for said infinite order AR model for said segments of said EEG signal as either:
 (a) the first autoregressive coefficient of said infinite order AR model; or
 (b) the difference of the sum of poles and the sum of zeros as determined respectively in steps (vi) and (vii)
(xi) determining an index value representing the activity of the brain for said segments of said EEG signal by applying a discriminating function to the sum of the poles of said infinite AR model for said segments of said EEG signal as determined in step (x); and
(xii) generating display data for displaying said index value on display means.

13. The system of claim 12 wherein the computing means provides the user of the system an option to select a time varying or time invariant ARMA signal representation in step (ii).

14. The system of claim 13 wherein the computing means carries out the steps of:
(xiii) selecting a fixed order time invariant ARMA signal representation of autoregressive order 8 and moving average order of 5;

$$y[n] = -\sum_{k=1}^{8} a_k y[n-k] + \sum_{k=0}^{5} b_k u[n-k]$$

where y[n] represents an ordinal sequence of samples of said EEG signal, y[n-k] represents the k-th prior sampled value of y[n]; u[n-k] represents a Gaussian white noise process; and $a_k$ and $b_k$ represent the estimated autoregressive AR and moving average MA coefficient data determined in step (iv) respectively for a said segment of said EEG signal
(xiv) estimating the autoregressive AR coefficients $a_1$-$a_8$ and moving average MA coefficients $b_0$-$b_5$ for the fixed order ARMA signal representation of the equation of step (ix) for one or more said EEG segments;
(xv) performing step (iii) on the equation of step (xiii) such that the z-domain representation is a z-domain equation;

$$Y(z) = \frac{\sum_{k=0}^{5} b_k z^{-k}}{\sum_{k=0}^{8} a_k z^{-k}} U(z)$$

(xvi) substituting estimated autoregressive AR and moving average MA coefficients into the z-domain equation of step (xv);
(xvii) performing step (v) on the z-domain equation of step (xv) using the equations;

$$\sum_{k=0}^{8} a_k p^{-k} = \sum_{k=0}^{8} a_k p^{8-k} = 0$$

$$\sum_{k=0}^{5} b_k z^{-k} = \sum_{k=0}^{5} b_k z^{5-k} = 0$$

wherein there are 8 poles each represented by the symbol p and wherein there are 5 zeros represented by the symbol z; and
(xviii) performing step (x) using either;

(a) $c_1 = -\sum_{i=1}^{i=8} z_{i,p} + \sum_{i=1}^{i=5} z_{i,z} \equiv -\langle z_p \rangle + \langle z_z \rangle$; or (b) $c_1 = a_1 - b_1$ wherein $z_{i,p}$ is the i-th pole, $z_{i,z}$ is the i-th zero and $a_1$ and $b_1$ are the first autoregressive and first moving average coefficient respectively of said time invariant ARMA signal representation and $c_1$ is the first coefficient of the infinite order AR model.

15. The system of claim 14 wherein the computing means carries out the steps of:
(xix) recursively estimating the autoregressive coefficients $a_1$-$a_8$ and moving average coefficients $b_0$-$b_5$ for each time instant n as $a_1^{(n)}$-$z_8^{(n)}$ and $b_0^{(n)}$-$b_5^{(n)}$ respectively so that the following fixed order time-varying ARMA representation will have been selected;

$$y[n] = -\sum_{k=1}^{8} a_k^{(n)} y[n-k] + \sum_{k=0}^{5} b_k^{(n)} u[n-k]; \text{ and}$$

(xx) calculating step (xviii)(b) using the equation $c_1^{(n)} = a_1^{(n)} - b_1^{(n)}$ wherein $a_1^{(n)}$ and $b_1^{(n)}$ are the first autoregressive and moving average coefficient respectively of said time varying ARMA representation of autoregressive order 8 and moving average order of 5 at time instant n.

16. The system of claim 12 wherein the computing means determines the index value to be a number in the range 0-100.

17. The system of claim 16 wherein the computing means determines the index value using the equation:

$$\text{index} = c - m\langle z_p \rangle$$

wherein c and m are constants selected such that the index value lies within said range and $\langle z_p \rangle$ is the sum of the poles of said infinite order AR model.

18. The system of claim 16 wherein the computing means determines the index value using the equation:

$$\text{index} = \frac{100}{1 + e^{-a(\langle z_p \rangle - b)}}$$

wherein a and b are constants selected such the index value lies within said range and $\langle z_p \rangle$ is the sum of the poles of said infinite order AR model.

19. The system of claim 12 wherein the computing means determines the index value using a scaling function determined by applying discriminant analysis to either the sum of the poles of said infinite order AR model.

20. The system of claim 12 wherein the index value is determined by combining the sum of the poles of said infinite order AR model with measures of cortical state and cortical input, that are also derived from the ARMA model and EEG data, using a function determined by applying disciminant analysis.

21. The system of claim 12 further including display means coupled to receive display data from the computing means and wherein the display means displays said index value in graphical form.

22. The system of claim 12 wherein the display means displays said index value in colours corresponding to different predetermined ranges of values of said index value, wherein each predetermined range is represented by a different colour.

* * * * *